(12) United States Patent
Trudel et al.

(10) Patent No.: US 6,544,210 B1
(45) Date of Patent: Apr. 8, 2003

(54) DISPOSABLE LAPAROSCOPIC SMOKE EVACUATION SYSTEM

(76) Inventors: Gregory J. Trudel, 10541 White Pine Dr., Parker, CO (US) 80134-2511; Shawn P. Smith, 30W181 Oxford Dr., Warrenville, IL (US) 60555-1013

( * ) Notice: Subject to any disclaimer, the term of this patent is extended or adjusted under 35 U.S.C. 154(b) by 0 days.

(21) Appl. No.: 09/177,202

(22) Filed: Oct. 22, 1998

(51) Int. Cl.[7] .............................................. A61M 37/00
(52) U.S. Cl. ......................................... 604/26; 604/28
(58) Field of Search ............................ 604/35, 319, 21, 604/23–28; 606/34; 206/363, 438–439; 95/214, 241–243, 254, 258, 273, 274, 286–287; 96/4, 7, 9, 176, 179, 182, 186, 202, 290, 296; 131/270–272, 202, 215.2, 331; 55/282, 284, 307, 308, 315–327, 338

(56) References Cited

U.S. PATENT DOCUMENTS

| | | | |
|---|---|---|---|
| 4,735,603 A | 4/1988 | Goodson et al. | 604/21 |
| 4,826,513 A * | 5/1989 | Stackhouse et al. | 96/131 |
| 4,986,839 A * | 1/1991 | Wertz et al. | |
| 5,047,072 A | 9/1991 | Wertz et al. | 55/1 |
| 5,108,389 A | 4/1992 | Cosmescu | 606/10 |
| 5,160,334 A | 11/1992 | Billings et al. | 606/34 |
| 5,234,428 A | 8/1993 | Kaufman | 606/45 |
| 5,246,419 A | 9/1993 | Absten | 604/26 |
| 5,336,169 A * | 8/1994 | Divilio et al. | |
| 5,417,655 A | 5/1995 | Divilio et al. | 604/22 |
| 5,578,000 A | 11/1996 | Greff et al. | 604/22 |
| 5,709,675 A * | 1/1998 | Williams | |

* cited by examiner

Primary Examiner—Brian L. Casler
Assistant Examiner—LoAn H. Thanh
(74) Attorney, Agent, or Firm—Jagtiani + Guttag

(57) ABSTRACT

A disposable laparoscopic smoke evacuation system. The system utilizes a small fan unit and filter housed in a single disposable housing adapted to be connected between two laparoscopic surgical instrument assemblies via tubing and powered by batteries or available AC power.

68 Claims, 4 Drawing Sheets

DISPOSABLE LAPAROSCOPIC SMOKE EVACUATION SYSTEM

FIELD OF THE INVENTION

The invention relates to surgical procedures and, more specifically, to a device and method for obtaining a smoke-free environment within the surgical field during laparoscopy.

BACKGROUND OF THE INVENTION

Laparoscopy is a fast growing surgical modality widely used in the treatment of certain prevalent physical ailments. Laparoscopy entails the introduction of an endoscope, light source and surgical instruments through ports formed in the patient's abdomen. In order to facilitate the procedure, the patient's abdominal cavity is inflated with a suitable gas to give the surgeon additional working area and minimize obstruction. Generally, laparoscopy avoids the risks of laparotomy, which requires the surgeon to open the abdomen and carry out the required procedure by his or her direct viewing.

The laparoscopic procedure is designed to avoid the surgical complications involved in a conventional laparotomy by allowing a surgeon to view the target site without opening up the patient's abdominal cavity. In a diagnostic laparoscopic procedure, only one channel is required through the patient's abdominal wall into the patient's abdominal cavity, into which the surgeon positions the laparoscope (laparoscopic camera) needed for viewing the underlying and overlying abdominal tissues and/or potential surgical field.

However, when the laparoscopic procedure requires tissue removal by ablation, several channels through the abdominal wall are required. These include a channel for the laparoscopic camera needed for viewing the surgical field, a channel for the laser or electrosurgical instrument used to burn the target tissue, a channel for insufflation (introduction of $CO_2$ gas into the patient's cavity to expand the patient's cavity) with $CO_2$ gas, and a means for withdrawal of gas and smoke. Note that insufflation with a suitable gas is required during the laparoscopic procedure so as to provide both increased cavity volume and optimal visual conditions during the surgical procedure. A smoke clearing system is usually employed in order to maintain both the visual clarity and proper abdominal pressure within the expanded cavity during the procedure.

A common procedure for positioning the laparoscopic assembly in the patient's abdominal cavity includes first making an incision into the patient's abdominal wall through which a large gauge needle is inserted. A suitable gas, typically $CO_2$, is then introduced into the patient's abdominal cavity through the needle. The needle is then replaced with a trocar, which is then removed leaving behind a sleeve, or cannula, through which a laparoscope is introduced into the abdominal cavity. In order to perform laser or electrosurgery one or two additional small incisions are made in the abdominal wall over the surgical site and cannula/trocar assemblies positioned accordingly. These cannula/trocar assemblies may be used for the positioning of the insufflation tube as well as any other surgical instruments that may be required for the particular laparoscopic procedure.

A laparoscopic procedure typically requires a surgeon to employ either electrosurgery or laser surgery within the confined space of the patient's abdominal cavity. This surgery typically involves tissue burning or ablation. This tissue burning leads to the creation of smoke. Surgical smoke within the confines of a patient's abdominal cavity reduces the surgeon's view of the surgical site, increases the patient's hematocrit levels, and causes delays in the surgery while the smoke is cleared from the laparoscopic field. Efficient removal of the smoke is thus a necessity for the surgical team during the laparoscopic procedure.

One method for removing smoke from the laparoscopic field is described in U.S. Pat. No. 4,735,603. This patent describes an elaborate and complex system for re-circulating and cleansing the smoke-laden gas produced inside a patient's abdominal cavity during a laparoscopic procedure. The system consists of a $CO_2$ gas pump that pumps gas into the patient's abdominal cavity by way of a solenoid control valve and a filter of such pore size as to remove bacteria size debris. Gas and smoke within the cavity are then evacuated by a return line, through a smoke clearing filter, a solenoid control valve, and a fluid trap before returning to the pump. A separate control module monitors the system for pressure variations and allegedly adjusts the pressure accordingly. The overall target cavity pressure is between 16–20 mm of Hg relative to atmospheric pressure. If the pressure exceeds 25 mm Hg or falls below 10 mm Hg the central control module closes the solenoid valves, which isolates the patient from the continued actions of the pump and allows the pressure to adjust accordingly. This system is large, cumbersome and can be costly.

Other laparoscopic smoke removal systems include: (1) suction devices which permit some air to be removed from the patient's cavity but require an equal input of gas back into the patient; (2) removal of smoke by opening a stopcock on one of the trocars, thus allowing the insufflation gas, laden with smoke, to be carried directly into the operating room; or (3) use of an adapted probe which can be inserted into the trocar for direct removal of smoke from the surgical site. Generally, the present systems are bulky, non-disposable, of complex design, are costly, and relatively large in size. Some devices also require connections to a house vacuum system within the surgical room. As such, it is unlikely that hospitals or health care offices that do not engage in numerous laparoscopic procedures will be able to justify the purchase of a conventional smoke removal system.

There is thus a need for a cost-effective solution to the removal of surgical smoke during a laparoscopic procedure.

There is also a need for a disposable, pre-sterilized smoke evacuation system that can be economically obtained and utilized by hospitals that do not routinely engage in laparoscopic procedures. It is with the above-referenced problems in mind that the present invention was developed.

SUMMARY OF THE INVENTION

The present invention is a smoke evacuation system utilizing a disposable inline gas pump/fan and filter apparatus comprising a housing defining an interior chamber and an inlet port and an outlet port. There is preferably an inline fan unit positioned in the interior chamber and a filter positioned in the interior chamber. The fan unit is preferably positioned between the inlet port and the filter. The apparatus has a power supply operably connected to the fan unit wherein the fan unit draws smoke-laden air from the patient's body cavity through the inlet port, past the fan, and pushes air through the filter, and the cleansed air is passed through the outlet port. Thereafter the cleansed air is re-introduced into the patient's cavity.

The present invention is connected between two laparoscopic cannula/trocar assemblies and works to eliminate surgical smoke and vapor, which has been created by the laser or other surgical devices, from the patient's abdominal, or other expanded body cavity during a laparoscopic procedure. The present invention comprises a small, portable, and disposable smoke clearing device which houses at least a fan unit and a filter media. Attached on one end of the smoke clearing device is a first flexible hollow tube attached to one of the cannula/trocar assemblies. Attached on the opposite end of the smoke clearing device is a second flexible hollow tube attached to the other cannula/trocar assembly, or other surgical device, inserted into the patient's abdominal or other body cavity.

The smoke clearing device is operated during a laparoscopic procedure to draw smoke from the surgical site out of the abdominal cavity, through the filter media, and return filtered gas back into the abdominal cavity. The present invention can best be understood by reference to the drawings and the detailed description below, wherein like parts are designated with like numerals throughout.

DETAILED DESCRIPTION OF THE INVENTION

Figure 1:
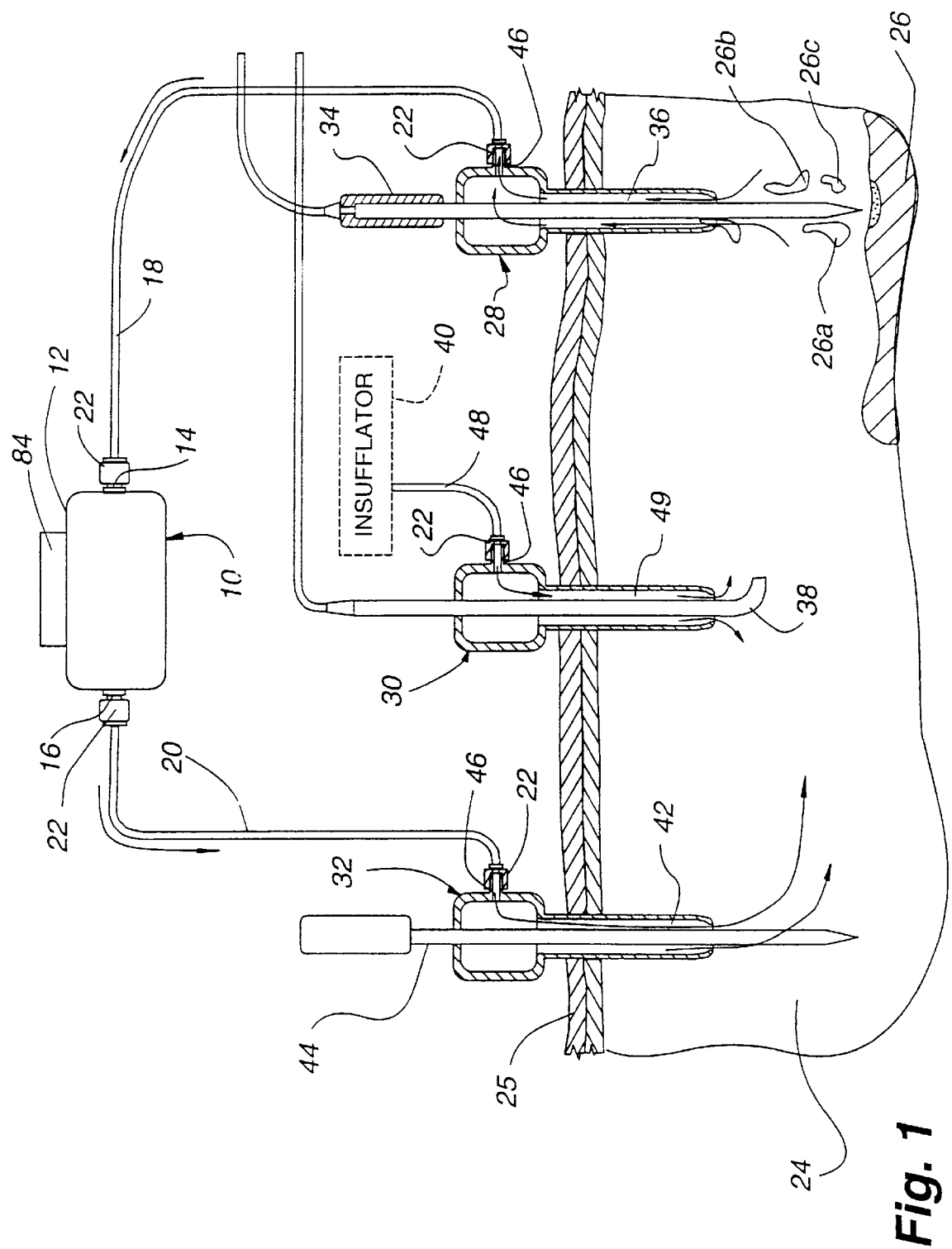
FIG. 1 is a schematic sectional view of a laparoscopic surgical site showing the input and evacuation cannula tubes, insufflation tube, electrosurgical instrument, and smoke clearing device in accordance with the present invention.

Referring to FIG. 1, the present invention is embodied in a smoke clearing device, 10 which includes a rigid housing 12, preferably defining three internal chambers (shown in later Figures). The housing 12 may be made out of a variety of materials, such as a metal or a plastic, as long as the material facilitates the device's use and is preferably disposable. The housing 12 preferably has a generally rectangular box shape or it may have a generally cylindrical hollow shape, preferably with rounded corners. The housing 12 contains an inlet port 14 at one end, i.e., on one side and an outlet port 16 at the other end, i.e., on the opposite side. One end of an inlet tube 18 is connected to the inlet port 14. One end of an outlet tube 20 is connected to the outlet port 16. This tubing is preferably conventional sterile flexible plastic tubing. It is envisioned that conventional Luer lock structures 22 will be used to connect the tubes 18 and 20 to the housing 12, but other locking structures could alternatively be used.

The patient's inner cavity, such as the abdominal cavity, is shown as 24 and the patient's skin is schematically shown as 25 in FIG. 1. The patient's tissue which is to be removed is shown as 26, with the surgical smoke shown and indicated as 26a, 26b and 26c. Three trocars containing laparoscopic surgical instrument clusters 28, 30 and 32 extend through the patient's skin 25 into the cavity 24.

These groups of instruments are representative of the type of instruments that are typically used in laparoscopic surgery. Each instrument cluster includes a cannula/trocar for introducing the instrument into the patient's cavity and maintaining a seal to the cavity 24 to preclude gas escape from the cavity 24. Each cannula/trocar has a single channel or passage along its length that allows instruments to be inserted into the body while maintaining the intra-abdominal pressure created by insufflation. Instrument cluster 28 is a single channel instrument cluster which serves to house the laser instrument 34 and direct the laser beam to the operating site. An annular channel 36 around the instrument 34 within the trocar serves as an annular egress passage from near the operating site for gas to be drawn around the laser instrument 34 and out of the patient's cavity to the smoke clearing device 10 of the present invention.

Instrument assembly 30 serves as a channel for the fiber optic laparoscopic camera and light 38 and also provides an annular inlet passage for the insufflation gas from an insufflator 40. The insufflator 40 may be a compressed gas cylinder and regulator valve assembly or a pump which supplies an initial volume of $CO_2$ gas. The other instrument assembly 32 provides both a channel 42 for the return of filtered re-circulated gas from the smoke clearing device 10 and may also may include an additional surgical instrument 44 which may be used for manipulating, dissecting or ablating tissues.

The outlet tubing 20 is connected at one end to the outlet port 16 of the device 10. The other end of the outlet tubing 20 is secured to the trocar/cannula of the instrument assembly 32 via a Luer lock assembly 22 to a valved port 46 on the trocar. Preferably a valved port 46 is provided with the Luer lock, although the valve portion may be omitted in some applications. The trocars have seals and flapper valves (not shown) within them to form a positive seal around the inserted instrument to maintain positive pressure within the body cavity 24 and preclude gas leakage from the cavity 24. Regardless of the presence or absence of a valved port, the connection between the tubing 20 and the instrument assembly 32 is to be sealed to outside air sources.

Similarly, the inlet tubing 18 is connected at one end to the inlet port 14 of the device 10. The other end of the inlet tubing 18 is secured to the trocar/cannula of the instrument assembly 28 via another Luer lock assembly 22 preferably to a valved port 46 on the trocar of the assembly 28. Again, the trocar has seals and flapper valves (not shown) within it to form a positive seal around the inserted instrument to maintain positive pressure within the cavity 24 and preclude gas leakage from the cavity 24.

During the laparoscopic procedure, gas from the patient's body cavity 24 is directed, as shown by the arrows, through the channel 36, out the port 46 in the instrument assembly 28, and through tubing 18 to the smoke clearing device 10. The unfiltered gas will then enter the smoke clearing device 10, be filtered, and will be returned to the patient's cavity 24 by way of the laparoscopic instrument assembly 32.

The laparoscopic port valve 46 allows for the smoke clearing device 10 to maintain a continuous flow of smoke out of the patient's cavity 24, or if preferred, to adjust the flow by simply manually conforming the valve so as to adjust the port diameter. Thus, it is within the scope of the present invention to be able to use the laparoscopic valve 46 on the instrument assembly 28 in a manner so as to control the suction pressure developed by the smoke clearing device 10. Note that the valve 46 is preferably designed not to close all the way so as to avoid undue vacuum pressure being drawn within the suction tubing 18 and/or in the smoke clearing device 10. Where a smaller level of suction is required the user has the ability to adjust the valve 46 so as to regulate the volume of gas being pulled toward the smoke clearing device. Alternatively, the valve 46 on the instrument assembly 32 may be throttled to adjust the flow rate through the device 10 back into the patient's abdominal cavity 24.

The tubing 20 is connected to the outlet port 16 of the smoke clearing device 10 preferably using a Luer lock assembly 22. The other end of the tubing 20 runs to the cannula/trocar of instrument assembly 32 where it is fitted into a valved port 46 via another Luer lock assembly 22. Again, and throughout this specification, all references to Luer locks herein are exemplary only. Any suitable connection mechanism may be utilized. The valved port 46 on the instrument assembly 32 communicates with an annular channel 42 which directs the returning gas back into the patient's cavity 24.

The insufflator 40 is connected to the trocar/cannula of instrument assembly 30 via tubing 48. The tubing 48 connects to a port 46 in the two chamber instrument assembly 30 by another Luer lock assembly 22. The cannula of the instrument assembly 30 extends through the patient's abdominal wall 25 into the cavity 24. The first or central channel provides a path for the laparoscopic camera and light 38 utilized to view the surgical field. The annular channel 49 around the laparoscope 38 provides a path for the $CO_2$ gas from the insufflator 40 into the patient's cavity 24.

As illustrated by arrows, the smoke clearing device 10 directs the flow of surgical smoke (26A, 26B and 26C) created during a laparoscopic procedure from the target site 26, through passage 36 in the laparoscopic assembly 28, through the laparoscopic port 46, into the tubing 18 and into the smoke clearing device 10. After flowing through the filter in device 10 the gas is returned to the target site by passing through tubing 20 and down the channel 42 of the cannula of the instrument assembly 32 to the cavity 24. Thus, the present embodiment is part of a closed system whereby the insufflation gas is filtered and re-circulated to maintain a constant level of gas in the patient's cavity 24.

There are connections between the laparoscopic assembly port and tubing, between the tubing and the smoke clearing inlet port, between the smoke clearing outlet port and tubing, and between tubing and the one channel cannula port. Each connection is preferably accomplished using a Luer lock as above described, but other known connections are envisioned. Each connection is envisioned as being sealed, but easily detachable when appropriate. FIG. 1 shows one embodiment of a surgical set up using the present invention. However, the present invention is not limited to a particular set up, and can be used with more or fewer instruments and tubing, depending on the surgeon's needs and the particular laparoscopic task at hand.

Note that the tubing is provided in a sterile form so as to limit the likelihood of infection at the surgical site. Additionally, these tubes preferably have smooth interior surfaces thereby reducing friction between the surgical smoke and the tubing walls, and are designed to be able to resist collapse from the forces exerted by the fan suction. The tubes may be constructed out of any of the plastic or rubber compositions commonly used for similar medical supplies.

Figure 2:
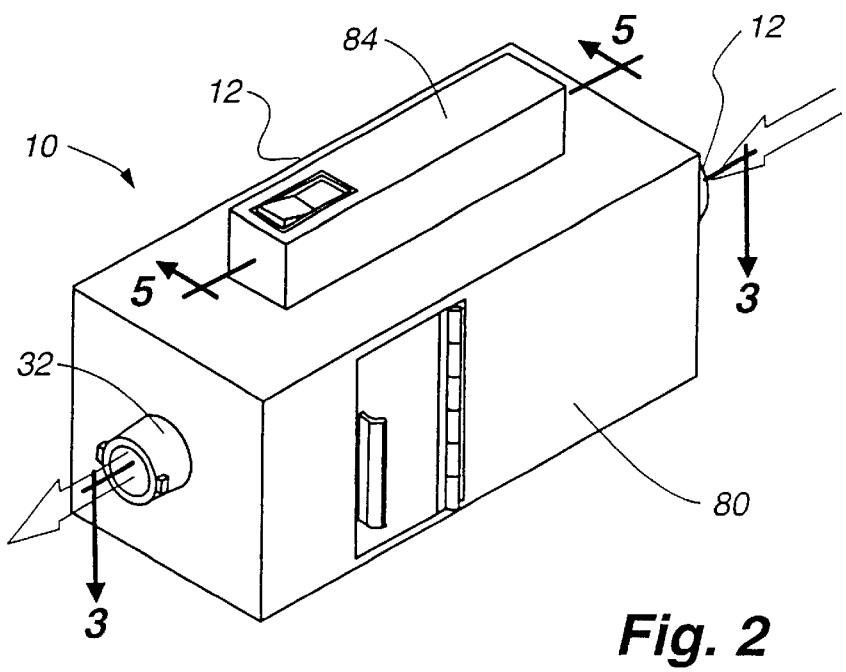
FIG. 2 is a perspective view of the smoke clearing device of the present invention.

FIG. 2 is a top view of the smoke clearing device 10. As indicated above, the device includes a rigid housing 12 defining an intermediate interior chamber 62 (shown in FIG. 3). A fan unit 54 is positioned within the intermediate interior chamber 64, as is a filter 56 (all shown in FIG. 3). A power source 58 is shown in communication with device 10.

Figure 3:
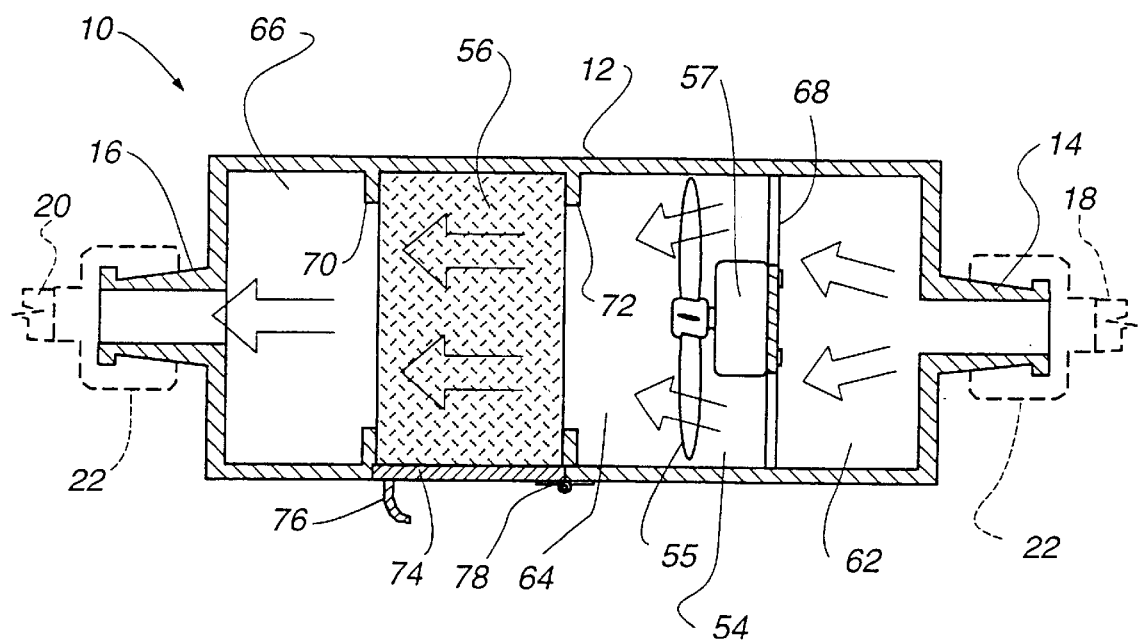
FIG. 3 is a section taken along line 3—3' of FIG. 2 of the components of the filter system in the smoke clearing device of the present invention.

FIG. 3 is a sectional view of one preferred embodiment of the smoke clearing device 10. The inlet end wall of the device 10 has an inlet port 14 connected to tubing 18 by a Luer lock 22. The smoke clearing device housing 12 preferably defines three chambers 62, 64, and 66, each of which is defined by the walls of the smoke clearing device housing 12 and by one of either the filter 56 or the fan mounting structure 68.

The anterior chamber 62 is defined by the smoke clearing device housing 12 and the fan mounting structure 68 supporting the fan unit 54. The anterior chamber 62 is continuous with the intermediate interior chamber 64, which is defined by the housing 12 of the smoke clearing device 10 and, at one end, the fan mounting structure 68 supporting the fan unit 54, and on the other end the filter 56. There is also an exhaust chamber 66 defined by the smoke clearing device housing 12 and one face of the filter 56. The interior wall surfaces of the smoke clearing device housing 12 are preferably smooth so as to reduce friction on the flow of gas. Gas flow, delivered by the action of the fan unit 54, enters the smoke clearing device 10 through the inlet port 14, travels through the anterior chamber 62 through the fan mounting structure 68, through the fan unit 54, to the intermediate interior chamber 64, through the filter 56, and out of the device 10 by way of the outlet port 16 in the end wall of the exhaust chamber 66.

The inline fan unit 54 is preferably positioned directly in the flow path of gas through the smoke clearing device 10. This direct, in-flow-path positioning provides for the maximum creation of vacuum pressure for sucking the surgical smoke from the patient's cavity 24 and advancing it through the smoke clearing filter 56. The fan blades 55 are driven by a fan motor 57 which is contained within a fan motor housing. The fan unit 54 is attached to the smoke filter device by way of a fan mounting structure 68. The fan mounting structure 68 is a narrow web support which is positioned in a plane normal to the base and longitudinal axis of the smoke filtering device 10 and spans the interior of the device so that the fan unit is stabilized through attachments to both the top and bottom of the device and/or its sides. The fan mounting structure 68 must have open space for the smoke to pass through. The fan mounting structure 68 preferably has a skeletal configuration so as to minimize restriction to gas flow such as a criss-cross or X-configuration of legs extending between the top and bottom of the smoke clearing device housing 12 or simply a series of three or more support legs extending transversely from the fan motor body to the outer walls of the housing 12.

Figure 6:
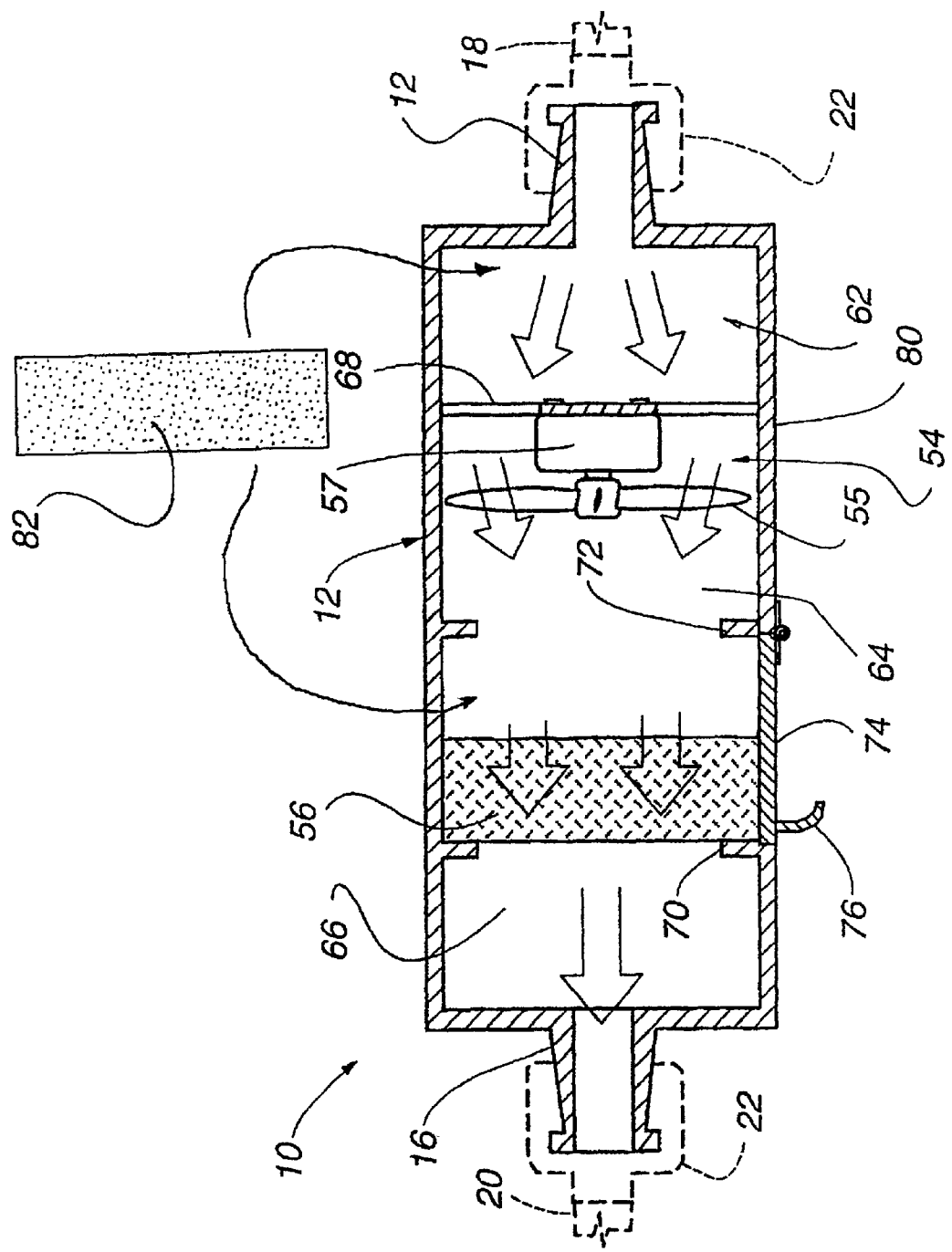
FIG. 6 is a section showing another alternative embodiment of the present invention.

It will be appreciated that the exact position of the fan unit 54 within the smoke clearing device 10 may be embodied in a number of configurations. For example, the fan unit can be positioned adjacent to the inlet port 14 in chamber 62 of the smoke clearing device 10, or it can be adjacent the filter 56, as is shown in FIG. 3. The fan unit 54 also may be positioned after or downstream of the filter 56, rather than before the filter 56 or it may also be positioned between the two filters as illustrated in FIG. 6. Additionally, the fan unit 54 may have any number of fan blades as long as the fan unit 54 is still of an effective capability to efficiently remove the surgical smoke generated during a procedure.

The fan unit 54 may be adjustable in speed. This would give the surgical personnel the ability to adjust the amount of suction applied to the laparoscopic field in a manner other than closing the laparoscopic port valve 46 as described above. Thus, dependent upon the amount of anticipated smoke or the volume of gas needed to be filtered, the appropriate fan speed could be selected.

The fan speed also may be adjusted depending on the type of filter which needs to be used. For example, if a filter with very small pores is used, the differential pressure generated across the filter will be higher and the fan speed may need to be increased accordingly. Alternatively, if a large pore size is used, the speed could be reduced. Finally, as the filter becomes clogged with contaminants the speed could be increased.

The surgical smoke is drawn through the inlet port 14 of the smoke clearing device 10 and into the anterior chamber 62 by the suction created by the fan unit 54. The fan unit 54 pulls the smoke through the blades 55 and pushes it into the intermediate interior chamber 64. Once on the front or downstream side of the fan unit 54, the smoke laden air is forced through the filter 56, into the exhaust chamber 66, and finally out of the smoke clearing device by way of outlet port 16.

FIG. 3 illustrates one embodiment of the filter system of the present invention. Smoke-laden gas is directed through a filter 56 located in the posterior chamber portion of the smoke clearing device 10. Preferably the filter 56 has a filtration capacity ranging from HEPA to ULPA specifications and is commercially available from a supplier such as Buffalo Filters, Buffalo, N.Y. The filter 56 is preferably held in place in the smoke clearing device 10 by a pair of spaced peripheral ribs 70 and 72 which project inward from the exterior walls of the smoke clearing device's housing 12. It is envisioned that the filter 56 is sealed to the inner edges of the ribs 70 and 72 in the smoke clearing device housing 12 so that no unfiltered air is allowed to pass through the device 10 without first being cleansed. Additionally, the filter 56 may come in a variety of widths and dimensions as long as the desired level of air cleansing is accomplished.

A filter access door 74 may optionally be provided in one of the side walls 80 of the housing 12. The filter access door 74 permits changing of the filter 56 as the differential pressure builds up across the filter due to buildup of contaminants. This door 74 preferably has a handle 76 of conventional design and may be hinged at hinge 78. The door 74 is preferably sealed by a suitable gasket material (not shown) to prevent gas leakage or air entry into the system during use. As is shown in FIGS. 2 and 3, the door 74 permits the filter 56 to be slid out of the housing 12 and easily replaced.

Figure 4:
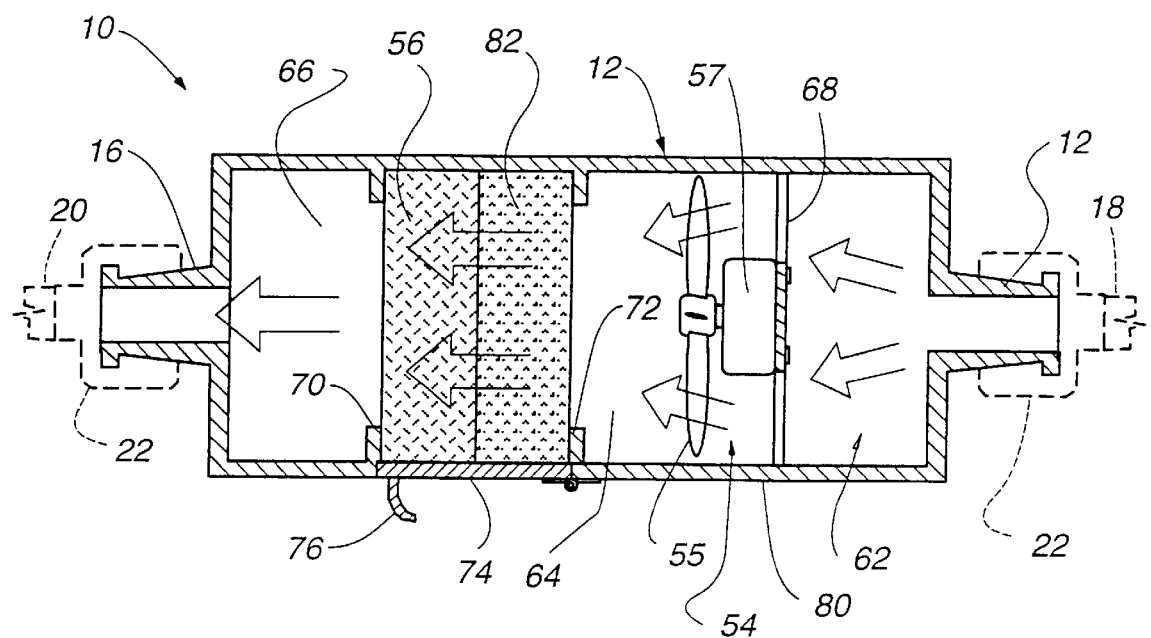
FIG. 4 is a section showing an alternative embodiment of the present invention.

An alternative embodiment of the filtering system illustrated in FIG. 3 is shown in FIG. 4, and includes a pre-filter 82 positioned before the primary filter 56. It is envisioned that the pre-filter 82 will have the exact same dimensions and orientation as does the primary filter 56. The pre-filter 82 has a larger diameter filter pore and is hydrophilic in nature. The pre-filter 82 would remove the larger smoke particles, particulates, and water vapor. The pre-filter 82 reduces the prevalence of filter clogging particulates in the primary filter 56. Once the surgical smoke has passed through the pre-filter 82, it enters the primary filter 56, which removes any remaining particulate debris from the air flow. Other embodiments are envisioned which may include adding additional filters in various configurations. Thus, there could be a single filter or a plurality of filters, depending upon the particular application. In addition, the fan unit 54 may be reverse driven to pull gas through the filter 56 in a direction opposite the arrows shown in FIGS. 3 and 4. In this instance, the tubing 18 and 20 would simply be connected in reverse, i.e., swapped between inlet port 14 and outlet port 16 so that the surgical smoke passes first through the filter or filters before reaching the fan unit.

Figure 5:
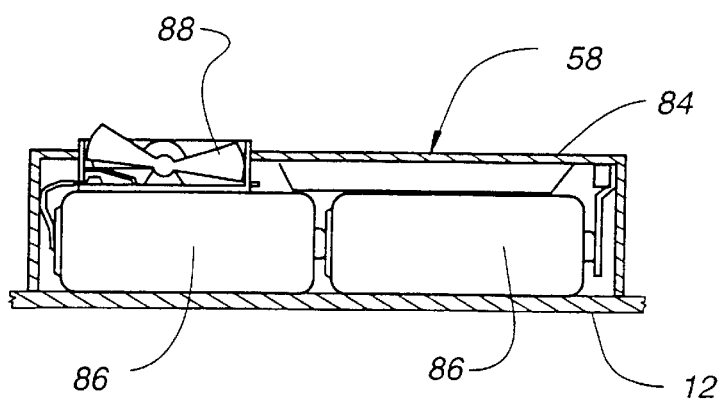
FIG. 5 is a cross-sectional view of a power supply for the present invention.

The power source 58 is preferably contained in a separate compartment 84 attached to the outside of the smoke clearing device housing 12. As shown in FIG. 5, the power source 58 preferably comprises a set of DC batteries 86 connected in series or parallel. A rocker, push button, or slide power switch 88 is positioned on the power source compartment 84 so that the user can electrically turn the device 10 on and off when appropriate. The smoke clearing device 10 is preferably turned "on" by depression of the switch and turned "off" by a second depression of the same switch. Alternatively, the switch can also be of a sliding configuration incorporating a variable power function that varies power to the fan to permit adjustment of fan speed and thus suction, flow rate, and gas throughput.

It can be appreciated that the power source 58 may also be comprised of two or more rechargeable DC or other type of batteries connected in series or in parallel. In this embodiment, a standard charging base, which contains a cord and plug to receive energy from a standard hospital wall electric outlet, would also be appropriate. Any other suitable power source which could power the device 10 may also be used.

The smoke clearing device 10 is self contained. Thus, the present invention eliminates any need for connection to a hospital vacuum system, or for that matter, a hospital power supply. As such, the device 10 may be used at health care facilities which do not contain in-house vacuum systems. Additionally, the device is advantageous in settings which do contain house vacuum systems where it is preferred that the in-house vacuum not be exposed to the surgical material introduced through the laparoscopic procedure.

The device 10 may also be configured with a clip device on the housing 12 and/or on the tubing 18 and 20 for securing the device 10 and tubing to the surgical drapes over the patient's body. Thus, from the foregoing description it can be appreciated that the present invention provides a sterile, portable, convenient, and relatively inexpensive alternative to those relatively cumbersome smoke evacuation systems of the prior art. It is also envisioned that the entire smoke clearing device could be packaged sterilely and sold in a sterile surgical kit form, which includes the housing with fan unit and filter(s) installed, tubing, and Luer locks (or other suitable tubing fasteners) in a sterile package. The power supply, in the kit form, could also include batteries in a separate package for installation and/or replacement during surgery as may be required.

Another alternative embodiment of the filtering system of the present invention, similar to the embodiment shown in FIG. 4 in many respects, is illustrated in FIG. 6 in which fan unit 54 is positioned between pre-filter 82 and primary filter 56.

The present invention is not intended to be limited to the particular embodiments illustrated but is intended to cover all such alternatives, modifications, and equivalents as may be included within the spirit and broad scope of the invention as defined by the following claims. All patents, patent applications, and printed publications referred to herein are hereby incorporated by reference in their entirety. The scope of the present invention is defined by the following claims.

What is claimed is:

1. A smoke removal apparatus comprising:

a housing;

inlet means for defining an inlet pathway for impure gas from a surgical cavity to said housing, wherein said inlet means comprise Luer locks for connecting said surgical cavity to said inlet pathway;

filter means for filtering impurities from impure gas to form filtered gas;

outlet means for defining an outlet pathway for said filtered gas from said housing to said surgical cavity; and a fan, for drawing impure gas from said surgical cavity, through said inlet means, and through said filter means to form said filtered gas and for driving said filtered gas through said outlet means into said surgical cavity, wherein said outlet means are adapted to laparoscopic surgical instrument assembly, wherein said filter means comprises a pre-filter and a primary filter with said pre-filter being positioned between said fan and said primary filter.

2. The apparatus according to claim 1, wherein said outlet means comprises Luer locks for connecting said outlet pathway to said surgical cavity.

3. The apparatus of claim 2, wherein said housing includes a pair of spaced peripheral internal ribs defining a sealable space in capable of receiving at least one of said primary filter and said pre-filter.

4. The apparatus according to claim 3, wherein said housing further comprises a side wall having an opening adjacent to said sealable space for insertion and removal of at least one of said group consisting of said primary filter and said pre-filter.

5. The apparatus according to claim 4, wherein said housing has a generally rectangular cross section with four side walls and a portion of each of said internal ribs extend inwardly from each of said four side walls.

6. The apparatus according to claim 5, wherein said fan operates at variable speeds.

7. The apparatus according to claim 4, further comprising a door over said opening of said side wall.

8. The apparatus according to claim 4, wherein a door is hinged to said side wall adjacent to said opening.

9. The apparatus of claim 2 wherein said inlet means comprises at least one inlet tube and said outlet means compromise at least one outlet tube.

10. The apparatus of claim 9, wherein said at least one inlet tube comprises a substantially sterile tube and said outlet tube comprises a substantially sterile tube.

11. The apparatus of claim 3, wherein said fan is adjustable in speed.

12. The apparatus of claim 2, wherein said fan is adjustable in speed.

13. The apparatus of claim 2, wherein at least one of said primary filter and said pre-filter is replaceable.

14. The apparatus according to claim 2, wherein said outlet means are adapted to a laparoscopic surgical instrument assembly.

15. The apparatus of claim 2, further comprising an intermediate chamber positioned between said fan and said filter means.

16. The apparatus of claim 2, wherein said filter means has a filtration capacity that meets HEPA specifications.

17. The apparatus of claim 2, wherein said filter means has a filtration capacity that meets ULPA specifications.

18. The apparatus of claim 2, wherein said filtered gas comprises substantially pure $CO_2$.

19. The apparatus of claim 1, wherein said housing includes a pair of spaced peripheral internal ribs defining a sealable space in capable of receiving at least one of said primary filter and said pre-filter.

20. The apparatus according to claim 19, wherein said housing further comprises a side wall having an opening adjacent to said sealable space for insertion and removal of at least one of said primary filter and said pre-filter.

21. The apparatus according to claim 8, wherein said housing has a generally rectangular cross section with four side walls and a portion of each of said internal ribs extend inwardly from each of said four side walls.

22. The apparatus according to claim 21, wherein said fan operates at variable speeds.

23. The apparatus according to claim 20, further comprising a door over said opening of said side wall.

24. The apparatus according to claim 20, wherein a door is hinged to said side wall adjacent to said opening.

25. The apparatus according to claim 19, wherein said fan is adjustable in speed.

26. The apparatus of claim 1, wherein said inlet means comprises at least one inlet tube and said outlet means comprises at least one outlet tube.

27. The apparatus of claim 24, wherein said at least one inlet tube comprises a substantially sterile tube and said outlet tube comprises a substantially sterile tube.

28. The apparatus of claim 1, wherein said fan is adjustable in speed.

29. The apparatus of claim 18, wherein at least one of said primary filter and said pre-filter is replaceable.

30. The apparatus of claim 1, further comprising an intermediate chamber positioned between said fan and said filter means.

31. The apparatus of claim 1, wherein said filter means has a filtration capacity that meets HEPA specifications.

32. The apparatus of claim 1, wherein said filter means has a filtration capacity that meets ULPA specifications.

33. The apparatus of claim 1, wherein said filtered gas comprises substantially pure $CO_2$.

34. A method for removing impurities from surgical cavity gas, using a smoke removal apparatus comprising:

a housing;

inlet means for defining an inlet pathway for impure gas from a surgical cavity to said housing, wherein said inlet means comprises Luer locks for connecting said surgical cavity to said inlet pathway;

filter means for filtering impurities from impure gas to form filtered gas;

outlet means for defining an outlet pathway for said filtered gas from said housing to said surgical cavity; and a fan, for drawing said impure gas from said surgical cavity, through said inlet means, and through said filtered gas and for driving said filtered gas through said outlet means into said surgical cavity, wherein said filter means comprises a pre-filter and a primary filter with said pre-filter being positioned between said fan and said primary filter;

wherein said surgical cavity is substantially enclosed and said method comprises the following steps:
removing said impure gas from said surgical cavity;
filtering said impurities from said impure gas to create filtered gas; and
returning said filtered gas to said surgical cavity.

35. The method of claim 34, wherein said filtered gas meets HEPA specifications.

36. The method of claim 34, wherein said filtered gas meets ULPA specifications.

37. The method of claim 36, wherein said filtered gas comprises substantially pure $CO_2$.

38. A method for removing impurities from surgical cavity gas, using a smoke removal apparatus comprising:

a housing;

inlet means for defining an inlet pathway for impure gas from a surgical cavity to said housing;

filter means for filtering impurities from impure gas to form filtered gas;

outlet means for defining an outlet pathway for said filtered gas from said housing to said surgical cavity, wherein said outlet means comprises Luer locks for connecting said outlet pathway to said surgical cavity; and a fan, for drawing impure gas from said surgical cavity, through said inlet means, and through said filter means to form said filtered gas and for driving said filtered gas through said outlet means into said surgical cavity, wherein said filter means comprises a pre-filter and a primary filter with said pre-filter being positioned between said fan and said primary filter;

wherein said surgical cavity is substantially enclosed and said method comprises the following steps:
removing said impure gas from said surgical cavity;
filtering said impurities from said impure gas to create filtered gas; and
returning said filtered gas to said surgical cavity.

39. The method of claim 38, wherein said filtered gas meets ULPA specifications.

40. The method of claim 39, wherein said filtered gas comprises substantially pure $CO_2$.

41. The method of claim 38, wherein said filtered gas meets HEPA specifications.

42. The method of claim 38, wherein said inlet means comprise Luer locks for connecting said surgical site to said inlet pathway.

43. A smoke removal apparatus comprising:

a housing;

inlet means for defining an inlet pathway for impure gas from a surgical cavity to said housing, wherein said inlet means comprises Luer locks for connecting said surgical cavity to said inlet pathway;

filter means for filtering impurities from impure gas to form filtered gas;

outlet means for defining an outlet pathway for said filtered gas from said housing to said surgical cavity; and a fan, for drawing said impure gas from said surgical cavity, through said inlet means, and through said filter means to form said filtered gas and for driving said filtered gas through said outlet means into said surgical cavity, wherein said outlet means are adapted to laparoscopic surgical instrument assembly, wherein said filter means comprises a pre-filter and a primary filter with said fan being positioned between said pre-filter and said primary filter.

44. The apparatus according to claim 43, wherein said outlet means comprises Luer locks for connecting said outlet pathway to said surgical site.

45. The apparatus of claim 44 wherein said inlet means comprises at least one inlet tube and said outlet means compromises at least one outlet tube.

46. The apparatus of claim 45, wherein said at least one inlet tube comprises a substantially sterile tube and said outlet tube comprises a substantially sterile tube.

47. The apparatus of claim 44, wherein said fan is adjustable in speed.

48. The apparatus of claim 44, wherein at least one of said primary filter and said pre-filter is replaceable.

49. The apparatus according to claim 44, wherein said outlet means are adapted to a laparoscopic surgical instrument assembly.

50. The apparatus of claim 44, wherein said filter means has a filtration capacity that meets HEPA specifications.

51. The apparatus of claim 44, wherein said filter means has a filtration capacity that meets ULPA specifications.

52. The apparatus of claim 44, wherein said filtered gas comprises substantially pure $CO_2$.

53. The apparatus of claim 43, wherein said inlet means comprises at least one inlet tube and said outlet means comprises at least one outlet tube.

54. The apparatus of claim 53, wherein said at least one inlet tube comprises a substantially sterile tube and said outlet tube comprises a substantially sterile tube.

55. The apparatus of claim 43, wherein said fan is adjustable in speed.

56. The apparatus of claim 43, wherein at least one of said primary filter and said pre-filter is replaceable.

57. The apparatus of claim 43, wherein said filter means has a filtration capacity that meets HEPA specifications.

58. The apparatus of claim 43, wherein said filter means has a filtration capacity that meets ULPA specifications.

59. The apparatus of claim 43, wherein said filtered gas comprises substantially pure $CO_2$.

60. A method for removing impurities from surgical cavity gas, using a smoke removal apparatus comprising:

a housing;

inlet means for defining an inlet pathway for impure gas from a surgical cavity to said housing, wherein said inlet means comprises Luer locks for connecting said surgical cavity to said inlet pathway;

filter means for filtering impurities from impure gas to form filtered gas;

outlet means for defining an outlet pathway for said filtered gas from said housing to said surgical cavity; and a fan, for drawing said impure gas from said surgical cavity, through said inlet means, and through said filter more to form filtered gas and for driving said filtered gas through said outlet means into said surgical cavity, wherein said filter means comprises a pre-filter and a primary filter with said fan being positioned between said primary filter and said pre-filter;

wherein said surgical cavity is substantially enclosed and said method comprises the following steps:
removing said impure gas from said surgical cavity;
filtering said impurities from said impure gas to create filtered gas; and
returning said filtered gas to said surgical cavity.

61. The method of claim 60, wherein said filtered gas meets ULPA specifications.

62. The method of claim 61, wherein said filtered gas comprises substantially pure $CO_2$.

63. The method of claim 60, wherein said filtered gas meets HEPA specifications.

64. A method for removing impurities from surgical cavity gas, using a smoke removal apparatus comprising:

a housing;

inlet means for defining an inlet pathway for impure gas from a surgical cavity to said housing;

filter means for filtering impurities from impure gas to form filtered gas;

outlet means for defining an outlet pathway for said filtered gas from said housing to said surgical cavity, wherein said outlet means comprises Luer locks for connecting said outlet pathway to said surgical cavity; and a fan, for drawing said impure gas from said surgical cavity, through said inlet means, and through said filter means to form said filtered gas and for driving said filtered gas through said outlet means into said surgical cavity, wherein said filter means comprises a pre-filter and a primary filter with said fan being positioned between said primary filter and said pre-filter;

wherein said surgical cavity is substantially enclosed and said method comprises the following steps:
removing said impure gas from said surgical cavity;
filtering said impurities from said impure gas to create filtered gas; and
returning said filtered gas to said surgical cavity.

65. The method of claim 64, wherein said filtered gas meets ULPA specifications.

66. The method of claim 65, wherein said filtered gas comprises substantially pure $CO_2$.

67. The method of claim 64, wherein said filtered gas meets HEPA specifications.

68. The method of claim 64, wherein said inlet means comprises Luer locks for connecting said surgical cavity to said inlet pathway.

\* \* \* \* \*